US00PP08257P

United States Patent [19]

Jessel, Jr.

[11] Patent Number: Plant 8,257

[45] Date of Patent: Jun. 15, 1993

[54] CARNATION PLANT NAMED CFPC CHALICE

[75] Inventor: Walter H. Jessel, Jr., Salinas, Calif.

[73] Assignee: California Florida Plant Co., L.P., Salinas, Calif.

[21] Appl. No.: 757,831

[22] Filed: Sep. 11, 1991

[51] Int. Cl.[5] ..... A01H 5/00

[52] U.S. Cl. ..... Plt./70.5

[58] Field of Search ..... Plt./70.2, 70.5, 70.6, Plt./71.1, 72.1

*Primary Examiner*—Howard J. Locker

*Attorney, Agent, or Firm*—Christie, Parker & Hale

[57] ABSTRACT

A new carnation of pink coloration.

1 Drawing Sheet

SUMMARY OF THE INVENTION

The present invention relates to a new and distinct variety of carnation plant which was originated by me in a controlled breeding program by my crossing as seed parent, an unnamed and unpatented seedling of my creation and as pollen parent, the variety known as 'Salmony' (varietal denomination 'Stasalm') (U.S. Plant Pat. No. 4,937). The varietal denomination of this new carnation is 'CFPC Chalice'.

Among the novel combination of characteristics possessed by the new variety which distinguishes it are attractive pink flower coloring and satisfactory early flowering response. Flowers of the new variety are produced on a very vigorous plant with strong, straight stems.

Asexual reproduction by propagation by side shoot cuttings of the new variety as performed in Fremont and Salinas, Calif., shows that the foregoing and other distinguishing characteristics come true to form and are established and transmitted through succeeding propagations. Although propagation by side shoot cuttings is described, other known methods of asexual reproduction may also be used to reproduce 'CFPC Chalice'.

BRIEF DESCRIPTION OF THE ILLUSTRATION

The accompanying illustration shows typical specimens of the vegetative growth and flowers of the new variety in different stages of development depicted in color as nearly true as it is reasonably possible to make the same in a color illustration of this character.

DESCRIPTION OF THE NEW VARIETY

The following is a detailed description of my new variety, with color terminology in accordance with The Royal Horticultural Society Colour Chart (R.H.S.C.C.). The terminology used in the color description herein refers to plate numbers in the aforementioned color chart. Color designations and color descriptions may deviate slightly from the stated values depending upon varying environmental, seasonal and cultural conditions.

The information provided herein is based on observations of plants grown inside commercial greenhouses at Fremont, Calif. The height of plant and flower and foliage size are established as an average using standard commercial cultural practices.

Name: CFPC Chalice.

Classification:

*Botanical.*—*Dianthus caryophyllus.*

*Commercial.*—Carnation, spray type.

Parentage:

*Female parent.*—Unnamed seedling (No. 870869).

*Male parent.*—'Salmony'.

Plant:

*Height.*—About 37 to 38 inches.

*Growing habit.*—Herbaceous, semi-upright.

*Blooming habit.*—Terminal as a spray.

*Blooming season.*—Year round.

*Rooting time.*—About 15-days.

*Mutation prone.*—Does not appear to be.

*Disease resistance.*—Unknown.

*Temperature tolerance.*—Wide range for carnation.

*Breaking action.*—Excellent.

Foliage:

*Color.*—Upper side: Near to 141A. Lower side: Near to 141C.

*Size.*—About 4½ to 5 inches long, about ⅓ inch wide at base of plant.

*Quantity.*—Numerous.

*Shape.*—Lanceolate.

*Texture.*—Smooth.

*Ribs.*—Central, keeled.

*Arrangement.*—Bi-lateral along stem.

*Stem color.*—Green.

Bud:

*Shape.*—Oval.

*Color.*—Green.

*Length.*—About 1 to 1¼ inches.

*Diameter.*—About ¼ to ⅜ inch.

Calyx:

*Numer of lobes (sepals).*—About 6.

*Length.*—About 1-inch.

*Width.*—About ¼-inch.

*Color.*—Outside — near to 141C. Inside — near to 145D.

Bloom:

*Shape.*—Round.

*Size.*—Diameter average: About 2¼ inches. Depth average: About 1 inch.

*Borne.*—Terminal as a spray.

*Color.*—General tonality: Light pink. Upper side: Near to from 65C to 56D. Lower side: Near to from 65C to 56D. Center: Near to 65C. Outer petals: Near to from 65C to 56D.

*Keeping quality.*—About 10 to 12 days.

*Fragrance.*—Slight.

*Permanence.*—Dry up on plant.

Petals:

*Number.*—About 46.

*Outer petals.*—Length: About 1 to 1¼ inches. Width: About ¾inch.

*Central petals.*—Length: About ¾-inch. Width: About ⅝ to ⅞-inch.

*Texture.*—Smooth.

*Form.*—Fan shaped.

*Appearance.*—Shiny.

Reproductive organs: Not visible in this variety.

*Stamens.*—Number: About 9 to 11. Arrangement: Around the ovary.

*Anthers.*—Length: About 3/16 to ¼-inch. Color: Near to 164C.

*Filaments.*—Length: About ¾ to 1-inch. Color: Near to 164D.

*Pistil.*—Number: About 3. Color: Near to from 62D to 65D. Length: About 1 to 1¼ inches.

*Stigma.*—Number: About 3.

*Ovary.*—Shape: Conical, ribbed. Color: Base — greenish white. Body — greenish yellow. Apex — tan.

I claim:

1. A new and distinct variety of carnation plant, substantially as shown and described.

* * * * *

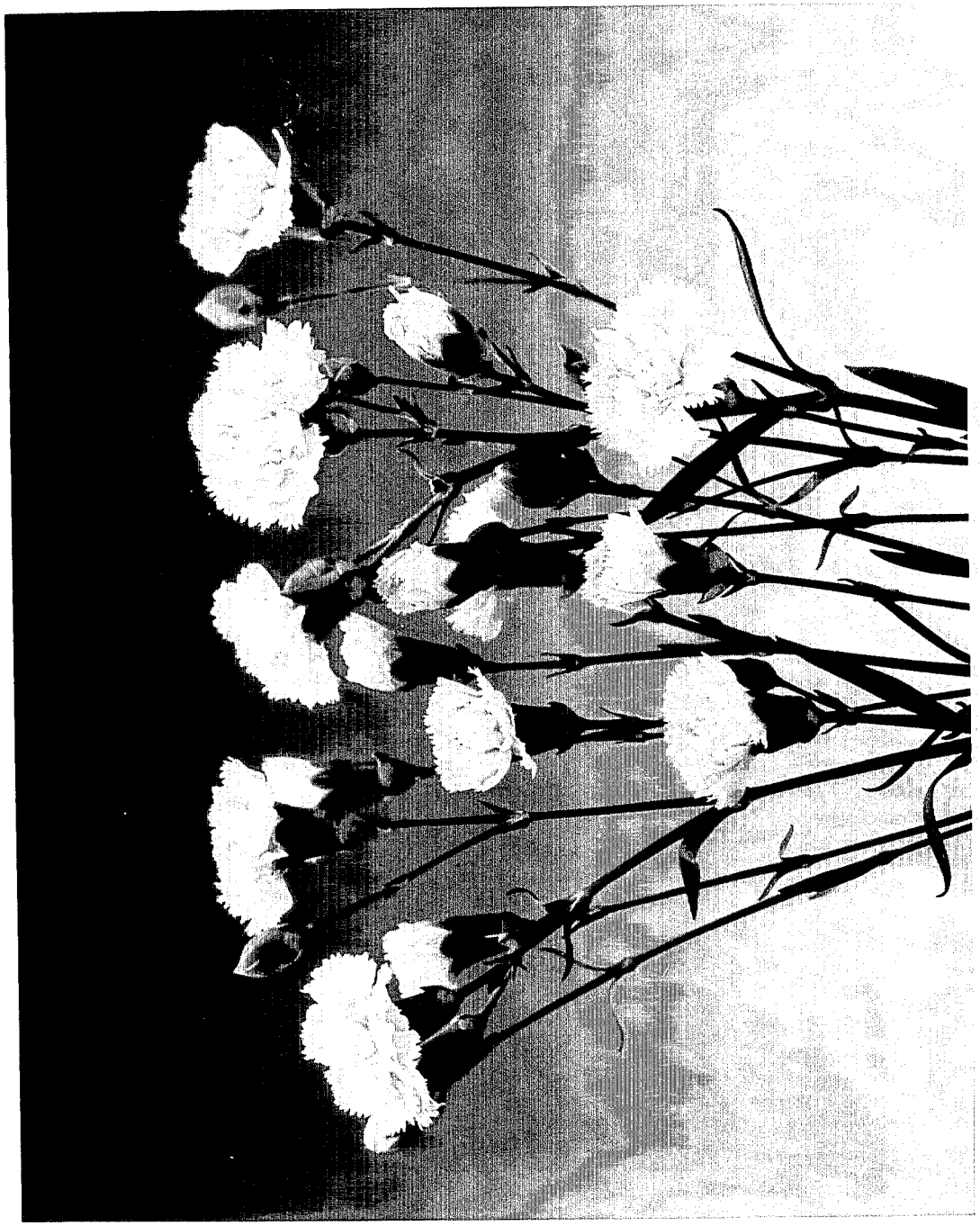

UNITED STATES PATENT AND TRADEMARK OFFICE

CERTIFICATE OF CORRECTION

PATENT NO. : Plant 8,257

DATED : June 15, 1993

INVENTOR(S) : Walter H. Jessel, Jr.

It is certified that error appears in the above-indentified patent and that said Letters Patent is hereby corrected as shown below:

Column 3, line 3, change "3/4inch" to -- 3/4-inch --.
Column 3, line 5, change "2/3" to -- 1/2 --.

Signed and Sealed this

Twenty-first Day of June, 1994

*Attest:*

Bruce Lehman

BRUCE LEHMAN

*Attesting Officer*

*Commissioner of Patents and Trademarks*